United States Patent [19]
Shima et al.

[11] Patent Number: 5,688,546
[45] Date of Patent: Nov. 18, 1997

[54] SEASONING MATERIAL

[75] Inventors: Keigo Shima; Tsutomu Harada; Eiichiro Suzuki; Yutaka Honda, all of Kawasaki, Japan

[73] Assignee: Ajinomoto Co., Inc., Tokyo, Japan

[21] Appl. No.: 504,136

[22] Filed: Jul. 19, 1995

[30] Foreign Application Priority Data

Jul. 19, 1994 [JP] Japan .................................. 6-166493
Sep. 21, 1994 [JP] Japan .................................. 6-226438
May 12, 1995 [JP] Japan .................................. 7-114603

[51] Int. Cl.$^6$ ......................................... A23L 1/22
[52] U.S. Cl. ...................... 426/534; 426/536; 426/537; 426/650; 426/656
[58] Field of Search .................... 426/534, 656, 426/536, 537, 538, 650

[56] References Cited

PUBLICATIONS

1973:147910 Document No. 78:147910, Bosin et al., J. Org. Chem., 38(8), 1591–600, 1973.
1982:616659 Document No. 97:216659, Hevelke et a. Monatsh. Chem., 113(4), 457–73, 1982.
1978:65968 Document No. 88:65968, Takayama et al., Japan Kokai JP 52102412 770827 Showa.
Database WPI, Derwent Publications, AN–79–39652b, JP–A–54–046857, Apr. 13, 1979.
Database WPI, Derwent Publications, AN–83–28625k, JP–A–58–024547, Feb. 14, 1983.
Database WPI, Derwent Publications, AN–88–194697, JP–A–63–132878, Jun. 4, 1988.
Chemical Abstracts, vol. 118, No. 19, May 10, 1993, AN–190283v.

*Primary Examiner*—Leslie Wong
*Attorney, Agent, or Firm*—Oblon, Spivak, McClelland, Maier & Neustadt, P.C.

[57] ABSTRACT

A seasoning composition containing food and an amino acid derivative that imparts a "thick, sour taste" to the food.

2 Claims, 4 Drawing Sheets

SEASONING MATERIAL

BACKGROUND OF THE INVENTION

1. Field of the Invention

The present invention relates to novel compounds which impart to foods a "thick, sour taste" even at neutral pH, compositions which contain such compounds, methods for preparing such compounds, and methods of flavoring food with such compounds.

2. Discussion of the Background

Natural extracts such as meat extract, chicken extract, extract of fishes and shells and vegetable extracts have been widely used commercially as basic seasonings of foods. It is considered that these natural extracts serve to give foods a complicated, deep, substantial taste, making up for an insufficient taste of certain food materials.

However, since these natural extracts are costly and hard to obtain, processed products and substitutes using a part of these natural extracts have been produced and marketed. Basic stocks of a dried bonito, dried small sardines, tangle and Cortinellus shiitake and flavor seasonings obtained by adding salt, sugar, flavor, amino acids and the like to these natural materials have been also widely used. These commercial processed products and substitutes of the natural extracts are made up of low-molecular weight substances such as amino acids (mainly sodium glutamate), nucleic acids and organic acids. Accordingly, compared with the natural extracts, these are defective in that the taste is plain and flat. In order to improve this defect, a substantial, complicated taste has been achieved so far by adding hydrolyzed vegetable protein (HVP), hydrolyzed animal protein (HAP), yeast extract, and the like. However, HVP and HAP have an odor resulting from the hydrolysis, and the yeast extract has an odor peculiar to the yeast. Accordingly, the amounts of these materials used are naturally limited, and the resulting taste and flavor are clearly different from the natural extracts. Therefore, these materials are not satisfactory, especially with respect to the "thick, sour taste" and the "sharp, deep taste" by which the overall taste of foods is improved.

SUMMARY OF THE INVENTION

Accordingly, it is one object of the present invention to provide novel compounds useful for providing a "thick, sour taste".

It is another object of the present invention to provide novel compounds useful for providing a "thick, sour taste" even at neutral pH.

It is another object of the present invention to provide a method of preparing such compounds.

It is another object of the present invention to provide flavoring compositions which contain such a compound.

It is another object of the present invention to provide a method of flavoring food by adding such a compound or composition to a food.

These and other objects, which will become apparent during the following detailed description, have been achieved by the inventors' discovery that fractions that give the "thick, sour taste" can be collected from a beef extract obtained by the treatment with hot water through a dialysis membrane, electrodialysis membrane, gel filtration chromatography, partition chromatography and reverse-phase chromatography, and the inventors' isolation of a novel amino acid derivative of formula (I) and having the below-mentioned properties.

The compound of formula (I) can be represented as any one of three tautomeric structures which are depicted as structural formulas (1), (2) and (3).

The inventors have also succeeded in synthesizing the novel amino acid derivative of formula (I) by using commercial reagents as starting materials through a chemical synthesis method and by mixing the commercial reagents and heating the mixture.

Molecular weight: 185

Molecular formula: $C_7H_{11}N_3O_3$

Structural formula:

(1) N-methyl-4-oxo-2-imidazolin-2-yl) alanine (Ia)

Structural formula:

(2) N-(1-methyl-4-oxo-imidazolidin-2,2-iridene)alanine (Ib)

Structural formula:

(3) N-(1-methyl-4-hydroxy-3-imidazolin-2,2-iridene) alanine (Ic)

Further, the inventors have discovered that when the isolated fraction of the novel amino acid derivative of formula (I) was concentrated, and an alcohol was then added thereto, and the mixture was allowed to stand at room temperature, colorless transparent laminar crystals were formed, and as a result of X-ray crystal structure analysis thereof, it was found that the compound of formula (I) was converted into the structural isomer of formula (II). The compound of formula (II) can be represented by any one of three tautomeric structures, which are depicted as structural formulas (4), (5), and (6).

Structural formula:

(4) N-(5-methyl-4-oxo-1-imidazolin-2-yl)sarcosine

(IIa)

Structural formula:

(5) N-(4-methyl-5-oxo-1-imidazolin-2-yl)sarcosine (IIb)

Structural formula:
(6) N-(4-methyl-5-hydroxy-2,5-imidazol-2-yl)sarcosine (IIc)

The inventors also found that in solution, part of the compound of formula (I) was ring-opened by hydrolysis to form the compound of formula (III) which can be represented by any one of two tautomeric structures which are depicted as structural formula (7) or (8).

Structural formula:
(7) N-[1-(N-carboxymethyl-N-methyl)amino-1-iminomethyl]alanine (IIIa)

Structural formula:
(8) N,N-[1-(N-carboxymethyl-N-methyl)amino-1-aminomethylidene]alanine (IIIb)

The inventors have also discovered that the compounds of formula (I), formula (II), formula (III), and formula (IV) also impart the "thick, sour taste."

(I)

wherein

X and Y are each N or NH,

Z is O or OH, (1) when X=N and Y=NH, Z=O, and *1 and *3 are double bonds, (2) when X=NH and Y=N, Z=O, and *2 and *3 are double bonds, (3) when X=N and Y=N, Z=OH, and *2 and *4 are double bonds, and R is selected from the group consisting of H, CH$_3$, CH$_2$CH$_2$COOH, CH$_2$CH$_2$CH$_2$CH$_2$NH$_2$, and CH$_2$CH$_2$CH$_2$CH$_3$;

(II)

wherein

X' and Y' are each N or NH,

Z' is O or OH, (1) when X'=NH and Y'=N, Z'=O, and *1 and *4 are double bonds, (2) when X'=N and Y'=NH, Z'=O, and *2 and *4 are double bonds, (3) when X'=N and Y'=N, Z'=OH, and *1 and *3 are double bonds, and R is as defined above;

(III)

wherein

X" is NH$_2$ or NH,

Y" is N or NH, (1) when X"=NH$_2$ and Y"=N, *2 is a double bond, (2) when X"=NH and Y"=NH, *1 is a double bond, and R is as defined above;

(IV)

wherein

X" is NH$_2$ or NH,

Y" is N is NH, (1) when X"=NH$_2$ and Y"=N, *2 is a double bond, (2) when X"=NH and Y"=NH, *1 is a double bond, and R is selected from the group consisting of —COCH$_2$—, —COCH$_2$CH$_2$—, —C(NH)NHCH$_2$CH$_2$CH$_2$—, and —CH$_2$CH$_2$CH$_2$CH$_2$—.

In addition, the inventors have found that hydrolysis of the compound of formula (I) affords the compound of formula (IV).

The present inventors have found that the compounds of the present invention, unlike other known organic and inorganic acids, give the sour taste even in the neutral pH region, and that if the compounds of the present invention are added to the processed products and substitutes of the existing natural extracts or to the basic stocks, it is possible to increase the seasoning power thereof, to improve the overall taste and to impart the "thick, sour taste" and the "deep taste". Further, the compounds of the present invention can reduce a heavy aftertaste and change it into a light taste by being added to foods having an unpleasant aftertaste.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The novel amino acid derivatives of the present invention may be added to the above-mentioned processed products and substitutes of the natural extracts or to the basic stocks to give such existing seasonings the "thick, sour taste". The present invention also provides a process for producing the processed products and substitutes of the natural extracts having a high-quality taste similar to those of the natural extracts, as well as a process for producing a high-quality basic stock.

The term "thick, sour taste" as used herein refers not to a sour taste that sharply stimulates the tongue, this sour taste being provided by organic acids (for example, citric acid, succinic acid, lactic acid and phosphoric acid) ordinarily used in food processing, but to a mild, sour taste, peculiar to the natural extracts, that spreads throughout the mouth.

The materials of the sour taste such as these organic acids and acidic amino acids, needless to say, do not exhibit the sour taste in the neutral pH region and cannot give the "thick, sour taste". Moreover, anserine, carnosine, creatine, creatinine, nucleic acids and saccharides which are known to exhibit seasoning properties do not exhibit the sour taste in the neutral pH region.

The animal and vegetable extracts which are used in the present invention are not particularly limited. Those ordinarily used in the food industry, such as beef, pork, chicken, fish, and the like can be optionally used. The substance that gives the "thick, sour taste" even in the neutral pH region can be also obtained by treating the yeast extract in like manner.

The novel amino acid derivatives that gives the "thick, sour taste" in the present invention can be formed, for example, by removing remains, precipitates, fats and oils from beef water extract or hot-water extract through a centrifugal separator or filter, then charging the extract into a commercial cellulose-type dialysis membrane, dialyzing the extract against water to remove high-molecular weight substances, and treating the dialyzate with an electrodialysis membrane or a column for gel filtration, partition chromatography, reverse-phase chromatography or the like.

Of course, the novel amino acid derivative of the present invention can be obtained by a synthesis method using creatinine, alanine or the like as a starting material. For example, the novel amino acid derivatives of the present invention, represented by the formula (I) may be synthesized by reacting creatinine with an α-halogeno carboxylic acid and/or its ester according to the following general synthesis scheme to produce the corresponding (ester) compound and, if needed, cleaving off the ester group by general methods of hydrolysis such as treatment with an alkaline reagent.

wherein R represents the side chain group of an α amino acid, R' is a $C_{1-4}$ alkyl, preferably methyl and Y denotes a halogen atom, preferably Br or Cl.

Some examples of reagents and the resulting a amino acid side chain groups are given in the following table:

| α-amino acid | Reagent | R |
| --- | --- | --- |
| alanine | methyl 2-bromopropionate | —$CH_3$ |
| glycine | ethyl bromoacetate | —H |
| lysine | methyl ε-benzoylamino-α-chlorocaprate | —$(CH_2)_4NH_2$ |
| glutamic acid | methyl α-chloroglutarate | —$(CH_2)_2CO_2H$ |
| leucine | methyl α-bromoisocaprate | —$(CH_2)_3CH_3$ |

The reaction between creatinine and the α-halogeno carboxylic acid or its ester may be carried out in a suitable solvent, for example dimethyl formamide, and in a broad temperature range from room temperature up to the reflux temperature of the solvent. A preferred temperature range is from about 30° to 80° C.

In order to obtain the structural isomers represented by formula (II), the compounds of formula (I) are dissolved under heating in a suitable solvent, for example a mixture of a lower alcohol (e.g. methanol or ethanol) and water and the compound is crystallized. According to the preferred example of the crystallization process the compound of formula (I) is dissolved in a mixture of methanol and water under heating. The obtained solution is set aside for several hours, preferably overnight, at room temperature to precipitate crystals having the structure of formula (II). The formed crystals are isolated by filtration and washed with methanol.

The compounds represented by formulae (III) and (IV) can be produced by hydrolysis under alkaline conditions. For example, the compound of formula (I) is converted into the compound of (III) by leaving the compound stand in 1N NaOH-solution overnight at room temperature.

It has been found that the thus-obtained novel amino acid derivative of the above-mentioned structure which has the molecular weight of 185 and which gives the "thick, sour taste" can be added to a stock of a Japanese food, for example, a stock of a dried bonito, chicken, fishes, shells, beef or Cortinellus shiitake, a soup stock of a Western food, for example, a stock of beef, chicken, pork, fishes or shells, or a soup of a Chinese food, for example, a stock of beef, chicken, pork, ham, eyes of scallop, ear shell, shrimp, dried cuttlefish, Cortinellus shiitake, Chinese cabbage or celery to increase the taste. Further, when the novel amino acid derivative is added to the processed products and substitutes of the natural extracts, especially, HVP, HAP and yeast extract which can be used as the amino acid mixture at relatively low cost, or to inexpensive beef extract, it deepens the whole taste, gives the "thick, sour taste" and increases the taste, providing the high-quality taste.

The optimum concentration of the novel amino acid derivative that gives the "thick, sour taste" varies depending on the foods and seasonings to which it is added. In any case, the compound of the present invention is added such that the concentration of it in solution becomes from 0.01 to 0.5% by weight (in terms of a solids content), whereby it is possible to provide the "thick, sour taste" which is lacking in the conventional stocks, to arrange the whole taste and to suppress the flat taste. Further, the compound of the present invention can effectively decrease the heavy aftertaste and change it into a light taste by being added to foods having an unpleasant aftertaste.

The novel amino acid derivative that gives the "thick, sour taste" in the present invention has a strong function of imparting the taste, and it can be used as a seasoning, added to processed foods, nutritious foods and medical foods and further effectively utilized as resources of marine products. This compound may be added as such or after having been dissolved in water.

Other features of the invention will become apparent in the course of the following descriptions of exemplary embodiments which are given for illustration of the invention and are not intended to be limiting thereof.

EXAMPLES

Preparation Example 1: Extraction

Approximately 6 kg of a beef shank meat were cut into cubes of from approximately 5 to 10 cm, charged into a 30 liter cylindrical aluminum pot, and boiled at from 90° to 95° C. for approximately 7 hours with the addition of 8 liters of water to obtain approximately 5 liters of a hot-water extract. The beef and precipitate formed were removed from the hot-water extract, and the residual extract was then refrigerated overnight. The oils, fats and precipitate formed during the refrigeration were further removed through a 60-mesh sieve. Further, the fine precipitate and solids were removed by a Sharples type ultra-centrifuge (15,000 rpm, manufactured by Nakamura Denki Seisakusho). The brown transparent supernatant obtained by the centrifugation was freeze-dried. The freeze-dried powder was dissolved in water to a concentration of 8 g/dl, and high-molecular weight substances were fully removed by means of an ultrafiltration membrane (fraction molecular weight=10,000). The thus-obtained low-molecular weight fraction solution was treated with an electrodialysis membrane (microdiaiyzer G3 manufactured by Asahi Chemical Industry Co., Ltd., membrane pore diameter molecular weight= approximately 1,000). The obtained outer solution (molecular weight=approximately 1,000 or less) was further treated with an electrodialysis membrane (membrane pore diameter molecular weight=approximately 100) to obtain an inner solution fraction which was a fraction of a beef, hot-water extract having a molecular weight of from approximately 100 to 1,000. The resulting solution was powdered by freeze-drying. In the treatment with the electrodialysis membrane, a point at which the conductivity and the current value of the dialyzate became zero was defined as a final point.

The thus-obtained fraction of the beef, hot-water extract having the molecular weight of from approximately 100 to 1,000 was subjected to various methods such as gel filtration chromatography (Sephadex G-25 column, 50×540 mm, manufactured by Pharmacia Biotek, eluent: 20 mM-ammonium acetate), partition chromatography (HPLC, TSKgel Carbon 500 column, 21.5×150 mm, manufactured by Tosoh Corp., eluent: 0.05% TFA→0.05% TFA/acetonitrile=50/50 gradient), and reverse-phase chromatography (HPCL, Capcellpak C18 UG120 column, 20×250 mm, manufactured by Shiseido Co., Ltd., eluent: 0.05% TFA→0.05% TFA/acetonitrile=50/50, gradient) to collect a substance that gives the "thick, sour taste".

The purity of the collected substance was measured by reverse-phase chromatography (HPLC, Ultron VX-ODS column, 4.6×250 mm, manufactured by Shinwa Kako K.K., eluent: 0.05% TFA →0.05% TFA/acetonitrile=50/50 gradient). As a result, the substance was found to be almost a single substance.

Analysis Example

The physicochemical properties of the substance that gives the "thick, sour taste" as obtained in the above-mentioned Preparation Example are as follows.

Results of analysis of the molecular weight:

The novel amino acid derivative obtained from the beef, hot-water extract by the above-mentioned method has the following properties.

Figure 1:
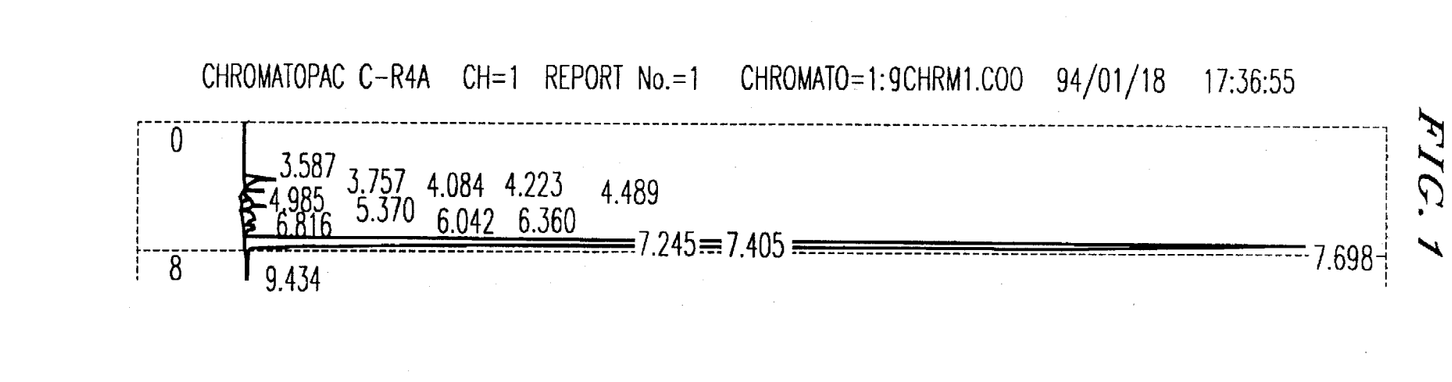
FIG. 1 is a Ultron VX-ODS column chromatography chart of an isolated sample obtained in Preparation Example 1.
Figure 2:
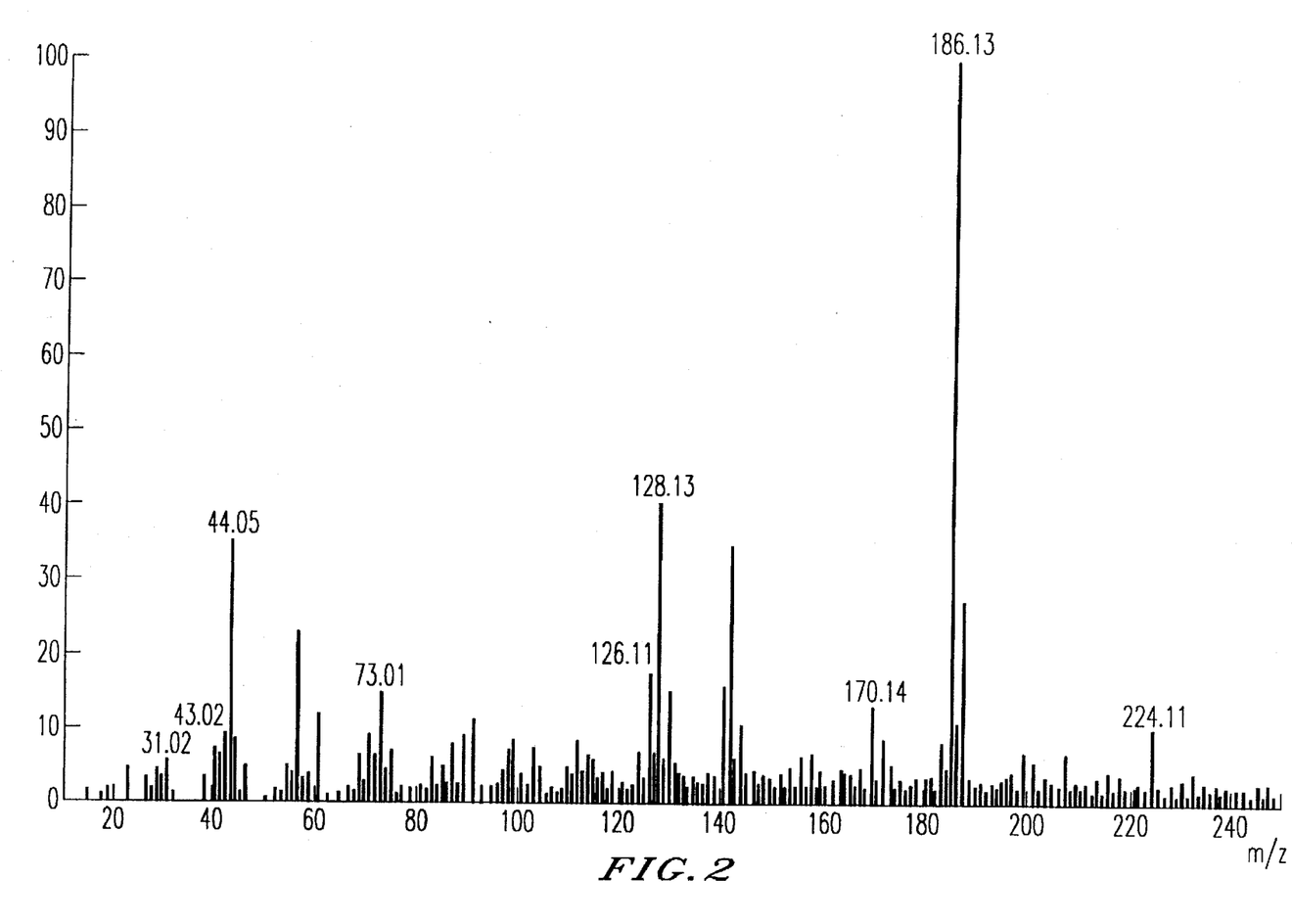
FIG. 2 is an FAB-MS chart of the isolated sample obtained in Preparation Example 1.

The molecular weight of the compound was found to be 185 as measured by fast atom bombardment analysis (hereinafter abbreviated as "FAB-MS"), and the results are shown in FIG. 2.

Figure 3:
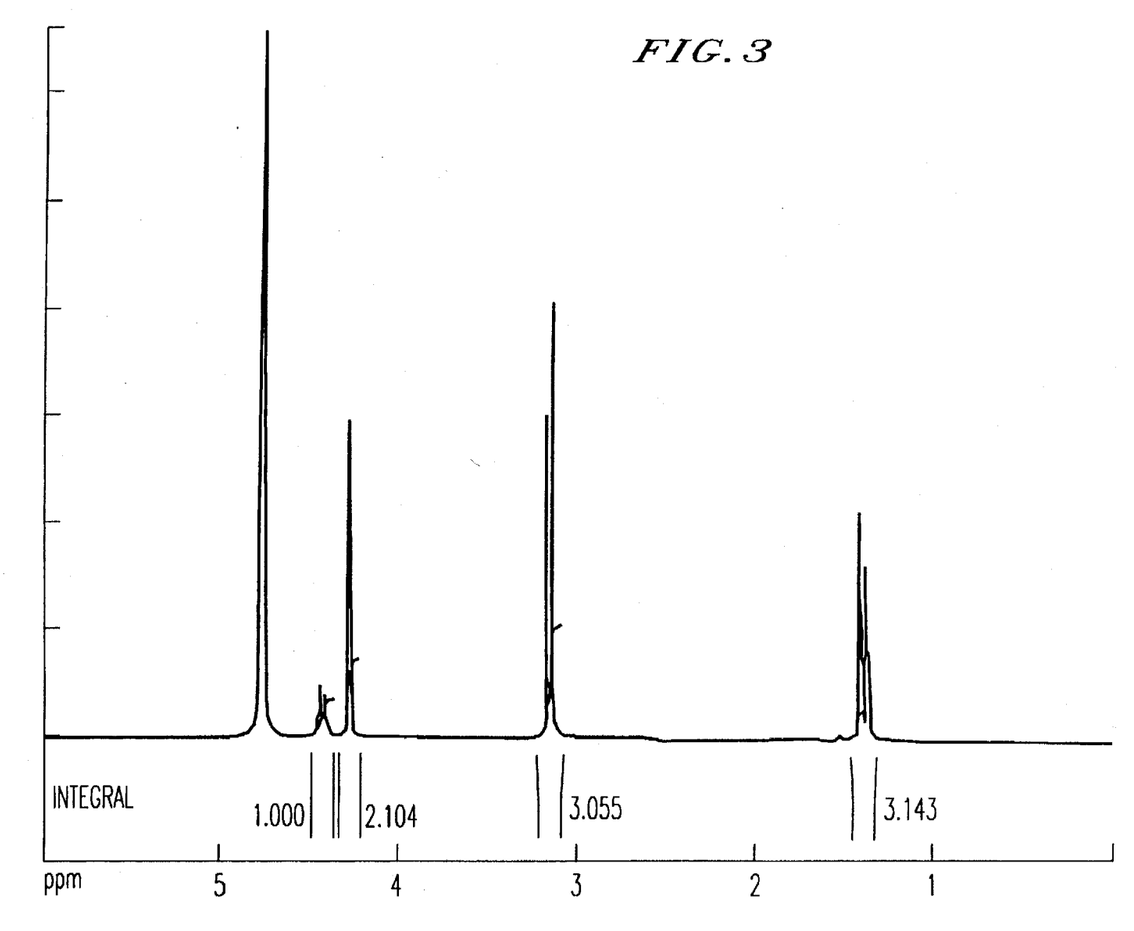
FIG. 3 is a ¹H-NMR chart of the isolated sample obtained in Preparation Example 1 (pH=approximately 2)
Figure 4:
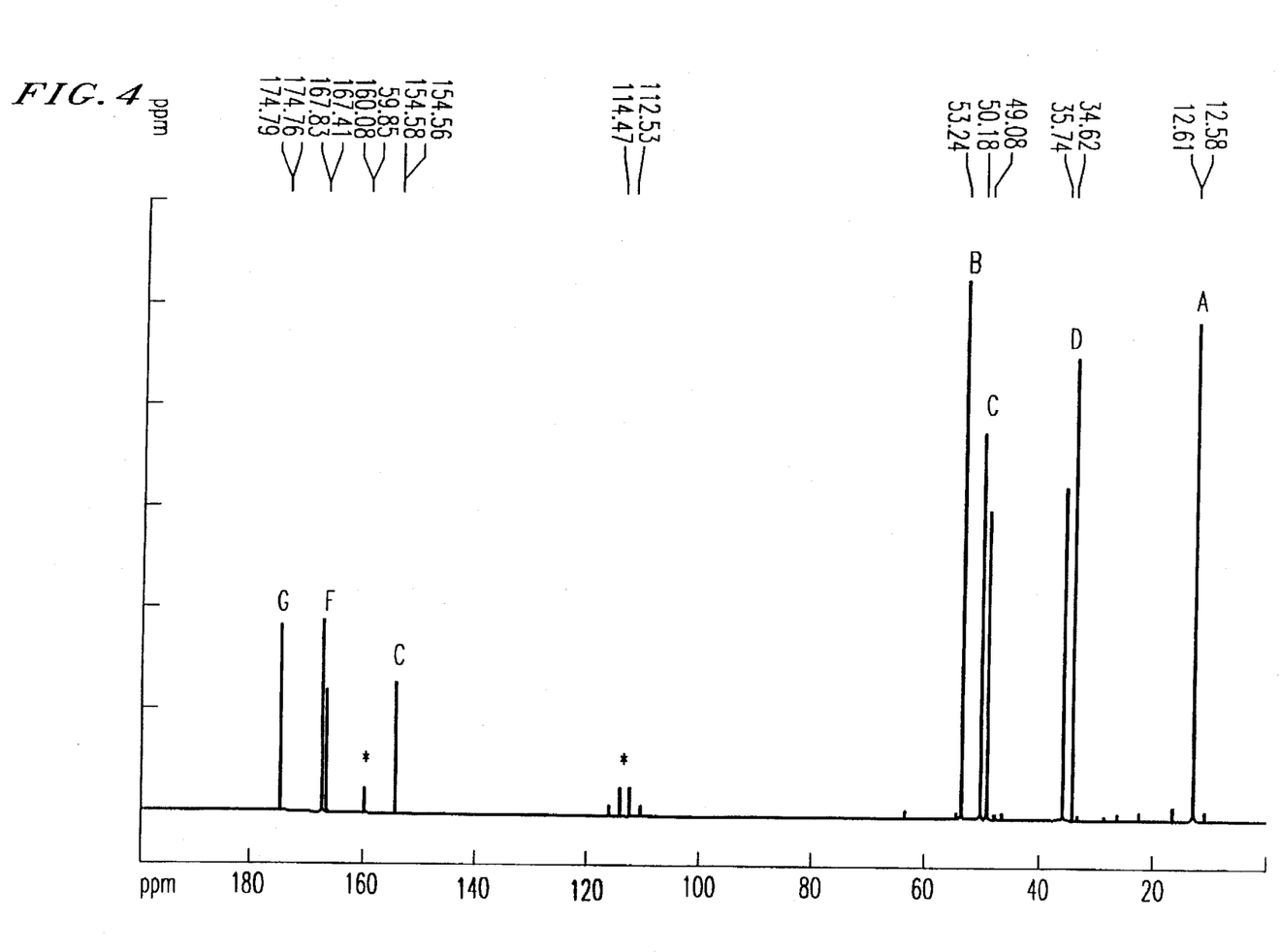
FIG. 4 is a ¹³C-NMR chart of the isolated sample obtained in Preparation Example 1 (pH=approximately 2).

Results of analysis of the molecular formula:

The molecular formula of the compound was determined to be $C_7H_{11}N_3O_3$ as measured by $^1$H-NMR and $^{13}$C-NMR, and the results are shown in FIGS. 3 and 4, respectively.

Results of analysis of the structural formula:

From the results of measurement by $^1$H-NMR and $^{13}$C-NMR, it was presumed that the skeleton of alanine or lactic acid was present and a skeleton similar to that of creatinine was present.

The novel amino acid derivative was deemed to be a condensed structure of the above-mentioned two moieties as measured by heteronuclear mutual remote bonding correlation (HMBC) analysis, and the above-mentioned structures (1), (2), and (3) were presumed. Incidentally, the compound of the present invention was found to be a set of structural isomers as measured by NMR spectrum.

Results of analysis of X-ray crystal structure:

Methyl alcohol was added to the concentrated solution of the compound of the present invention in an amount of approximately 4 volumes, and the mixture was allowed to stand at room temperature. A few days later, colorless transparent laminar crystals were precipitated, and then filtered under reduced pressure to collect crystals. The crystals were subjected to X-ray crystal structure analysis. As a result, the crystals were found to have the above-mentioned structures (4), (5), and (6). That is, it was found that the structures (1), (2), and (3) were changed into the structures (4), (5), and (6) of the structural isomers by the crystallization.

Evaluation of a function of imparting the "thick, sour taste":

The function of imparting the "thick, sour taste" which was provided by the thus-obtained novel amino acid derivative was evaluated by adding the novel amino acid derivative to a commercial consomme soup such that the solids content became 0.05% by weight in terms of a solids content. Profile evaluation of the function was conducted by five panelists. As a result, it was found that the sample containing the novel amino acid derivative imparted the "thick, sour taste" to the commercial consomme soup.

Further, in order to measure the suitable amount of the novel amino acid derivative added, the novel amino acid derivative was added to the commercial consomme soup in an amount of 0.01% by weight, 0.03% by weight, 0.05% by weight, 0.1% by weight, 0.2% by weight or 0.5% by weight (in terms of a solids content). The suitable amount of the novel amino acid derivative added was evaluated by the panelists. As a result, it was found that the sample containing the novel amino acid derivative increased the substantial, thick taste without changing the flavor of the commercial consomme soup as a control, and that it deepened the whole taste and gave the "thick, sour taste". However, with the addition of 0.2% or more of the novel amino acid derivative, no big difference was found. From the economical standpoint, the amount of approximately 0.05% by weight was estimated to be sufficient.

In this manner, the novel amino acid derivative was added to the commercial consomme soup, and the organoleptic evaluation was conducted. The mixing ratio was as follows. That is, hot water was added to one cube (5 g) of the commercial consomme soup and 0.3 g of the novel amino acid derivative powder of the present invention such that the total amount was 300 ml.

As a control, a consomme soup not containing the novel amino acid derivative was prepared. The two types of the soups were subjected to the organoleptic evaluation by 20 taste panelists through a 2-point comparison method. The results are shown in Table 1.

TABLE 1

|  | Soup containing the novel amino acid derivative | Control soup |
| --- | --- | --- |
| Preferable flavor | 13 | 7 |
| Preferable taste | 12 | 8 |
| "Thick, sour taste" which is stronger. | 18* | 2 |
| Lighter aftertaste | 18* | 2 |
| More complicated taste | 17* | 3 |
| Preferable as a whole | 17* | 3 |
| Remarks | Unpleasant aftertaste is decreased, and the taste becomes light | Nothing particular |

*Level of significance is 5% with an appreciable difference.

Preparation Example 2: Chemical synthesis

Seventy grams of reagent grade creatinine (made by Nacalai Tesque Co.) and 114 ml of reagent grade methyl-2-bromopropionate (made by Merck Japan) were used as starting materials, and approximately 15 grams of the above-mentioned novel amino acid compound were obtained as schematically shown below. The structure of the obtained compound was analyzed by the above-mentioned FAB-MS, $^1$H-NMR and $^{13}$C-NMR, and was then found to be the same as the structure of the compound obtained from the beef, hot water extract. At this time, the yield of the compound was approximately 12 mol %.

Preparation Example 3: Heat-formation

A 0.5-M solution of reagent grade creatinine (made by Nacalai Tesque Co.,) and a 0.5-M solution of alanine (made by Ajinomoto Co., Inc.) were heated at a pH of 10 for 30 hours. The obtained reaction solution was treated with a DEAE TOYOPEARL (11.2 cm×20 cm) column to remove unreacted creatinine and alanine. At this time, the eluent was 20-mM ammonium acetate, the flow rate was 18.5 ml/min, and the detection was conducted with absorbance at 280 nm. The content of the novel amino acid derivative in each fraction was analyzed by a Carbon 500 column. Further, the fraction containing this novel amino acid derivative was collected and concentrated. Subsequently, the novel amino acid derivative was singly collected by means of a Carbon 500 column for collection. The structure of the obtained compound was analyzed by the above-mentioned FAB-MS, $^1$H-NMR and $^{13}$C-NMR, and it was found to be the same as that of the compound obtained from the beef, hot-water extract.

Evaluation of a function of imparting the "thick, sour taste":

It was confirmed that both of the novel amino acid derivatives prepared by the chemical synthesis and the heat-formation had the same function of imparting the "thick, sour taste" as the novel amino acid derivative isolated from the beef, hot-water extract.

Preparation Example 4: Crystallization

The compounds of formula (I) are converted into the compounds of formula (II) by crystallization.

An example of the crystallization conditions is as follows:

100 mg of the syrup-like compound obtained by the preparation Example 2 was dissolved in a mixture of 200 ml of methanol with 50 mol of water under heating. The obtained solution was set aside overnight at room temperature to precipitate crystals having the structure of formula (II) (R: CH$_3$). The formed crystals were washed with methanol and then filtrated to obtain white crystals.

Preparation Example 5: Hydrolysis

Production method of the compounds of formula (III):

The compounds of formula (III) can be produced by hydrolyzation under alkali conditions. For example, the compound of formula (I) is converted into the compound of formula (III) by setting aside the compound of formula (I) in 1N NaOH solution overnight at room temperature.

Preparation Example 6: Hydrolysis

Production method of the compounds of formula (IV):

The compounds of formula (IV) can be produced by hydrolyzation under alkali conditions. For example, the compound of formula (I) is converted into the compound of formula (IV) by setting aside the compound of formula (I) in 1N NaOH solution overnight at room temperature.

The seasoning material containing the novel amino acid derivative of the present invention is added to processed products and substitutes of natural extracts or basic stocks, whereby the "thick, sour taste" can be given to these existing seasonings to provide the processed products and substitutes of the natural extracts or the basic stocks that give the high-quality taste similar to the taste of the natural extracts.

This application is based on Japanese patent applications 166493/1994, filed Jul. 19, 1994; 226438/1994, filed Sep. 21, 1994; and 114603/1995, filed May 12, 1995, all of which are incorporated herein by reference in their entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A seasoning composition comprising food containing an effective amount of a compound selected from the group consisting of formula (I), formula (II), formula (III), and formula (IV):

(I)

wherein
X and Y are each N or NH,
Z is O or OH,
(1) when X=N and Y=NH, Z=O, and *1 and *3 are double bonds,
(2) when X=NH and Y=N, Z=O, and *2 and *3 are double bonds,
(3) when X=N and Y=N, Z=OH, and *2 and *4 are double bonds, and
R is selected from the group consisting of H, $CH_3$, $CH_2CH_2COOH$, $CH_2CH_2CH_2CH_2NH_2$, and $CH_2CH_2CH_2CH_3$;

(II)

wherein
X' and Y' are each N or NH,
Z' is O or OH, (1) when X'=NH and Y'=N, Z'=O, and *1 and *4 are double bonds,
(2) when X'=N and Y'=NH, Z'=O, and *2 and *4 are double bonds,
(3) when X'=N and Y'=N, Z'=OH, and *1 and *3 are double bonds, and
R is as defined above;

(III)

wherein
X" is $NH_2$ or NH,
Y" is N or NH,
(1) when X"=$NH_2$ and Y"=N, *2 is a double bond,
(2) when X"=NH and Y"=NH, *1 is a double bond, and
R is as defined above; and (IV)

wherein
X" is $NH_2$ or NH,
Y" is N or
(1) when X"=$NH_2$ and Y"=N, *2 is a double bond,
(2) when X"=NH and Y"=NH, *1 is a double bond, and
R' is selected from the group consisting of —$COCH_2$—, —$COCH_2CH_2$—, —$C(NH)NHCH_2CH_2CH_2$—, and —$CH_2CH_2CH_2CH_2$—.

2. A method of seasoning food, comprising adding to food a compound selected from the group consisting of formula (I), formula (II), formula (III), and formula (IV):

(I)

wherein
X and Y are each N or NH,
Z is O or OH,
(1) when X=N and Y=NH, Z=O, and *1 and *3 are double bonds,
(2) when X=NH and Y=N, Z=O, and *2 and *3 are double bonds,
(3) when X=N and Y=N, Z=OH, and *2 and *4 are double bonds, and
R is selected from the group consisting of H, $CH_3$, $CH_2CH_2COOH$, $CH_2CH_2CH_2CH_2NH_2$, and $CH_2CH_2CH_2CH_3$;

(II)

wherein

X' and Y' are each N or NH,
Z' is O or OH,
(1) when X'=NH and Y'=N, Z'=O, and *1 and *4 are double bonds,
(2) when X'=N and Y'=NH, Z'=O, and *2 and *4 are double bonds,
(3) when X'=N and Y'=N, Z'=OH, and *1 and *3 are double bonds, and
R is as defined above;

(III)

wherein
X" is NH₂ or NH,
Y" is N or NH,
(1) when X"=NH₂ and Y"=N, *2 is a double bond,
(2) when X"=NH and Y"=NH, *1 is a double bond, and
R is as defined above; and (IV)

wherein
X" is NH₂ or NH,
Y" is N or NH,
(1) when X"=NH₂ and Y"=N, *2 is a double bond,
(2) when X"=NH and Y"=NH, *1 is a double bond, and
R' is selected from the group consisting of —COCH₂—, —COCH₂CH₂—, —C(NH)NHCH₂CH₂CH₂—, and —CH₂CH₂CH₂CH₂—.

* * * * *